United States Patent
Jani et al.

(10) Patent No.: US 9,682,904 B2
(45) Date of Patent: Jun. 20, 2017

(54) PROCESS FOR SEPARATING BENZENE FROM A REACTOR EFFLUENT

(71) Applicant: UOP LLC, Des Plaines, IL (US)

(72) Inventors: Priyesh Jayendrakumar Jani, Haryana (IN); Soumendra M. Banerjee, New Delhi (IN)

(73) Assignee: UOP LLC, Des Plaines, IL (US)

( * ) Notice: Subject to any disclaimer, the term of this patent is extended or adjusted under 35 U.S.C. 154(b) by 355 days.

(21) Appl. No.: 14/202,526

(22) Filed: Mar. 10, 2014

(65) Prior Publication Data

US 2015/0251978 A1    Sep. 10, 2015

(51) Int. Cl.
*C07C 7/04* (2006.01)

(52) U.S. Cl.
CPC ....................... *C07C 7/04* (2013.01)

(58) Field of Classification Search
CPC .................. C07C 7/04; C10G 49/22
See application file for complete search history.

(56) References Cited

U.S. PATENT DOCUMENTS

| | | | | |
|---|---|---|---|---|
| 6,159,272 | A * | 12/2000 | Baker ................. | B01D 53/002 95/39 |
| 2010/0228063 | A1* | 9/2010 | Almering ................. | C07C 7/04 585/264 |
| 2011/0147270 | A1 | 6/2011 | Goldstein et al. | |
| 2013/0193034 | A1 | 8/2013 | Bourane et al. | |
| 2013/0228447 | A1* | 9/2013 | Wu .......................... | B01D 3/40 203/28 |

FOREIGN PATENT DOCUMENTS

WO     WO 03/012011 A1    2/2003

OTHER PUBLICATIONS

Thom et al., "Consider advanced technology to remove benzene from gasoline blending pool," Hydrocarbon Processing (Feb. 2013), 75-77, vol. 92.
Netzer et al., "Benzene Recovery from Refinery Sources by Co-production of Olefins," NPRA Annual Meeting (Mar. 23, 2003), San Antonio, Texas US.

* cited by examiner

*Primary Examiner* — Sharon Pregler
*Assistant Examiner* — Alyssa L Cepluch

(57) ABSTRACT

A process for separating benzene from a reactor effluent in which the reactor effluent is passed to a first separation zone to separate the effluent into a bottom benzene lean stream and an overhead stream. The bottom benzene lean stream does not need to be processed further to remove benzene. The overhead stream may be cooled and is passed to a second separation zone in which it is separated into a bottom benzene rich stream and a second overhead stream. The bottom benzene rich stream contains at least 80% of the benzene from the reactor effluent. The operating temperature of the first separation zone is greater than the operating temperature of the second separation zone.

14 Claims, 1 Drawing Sheet

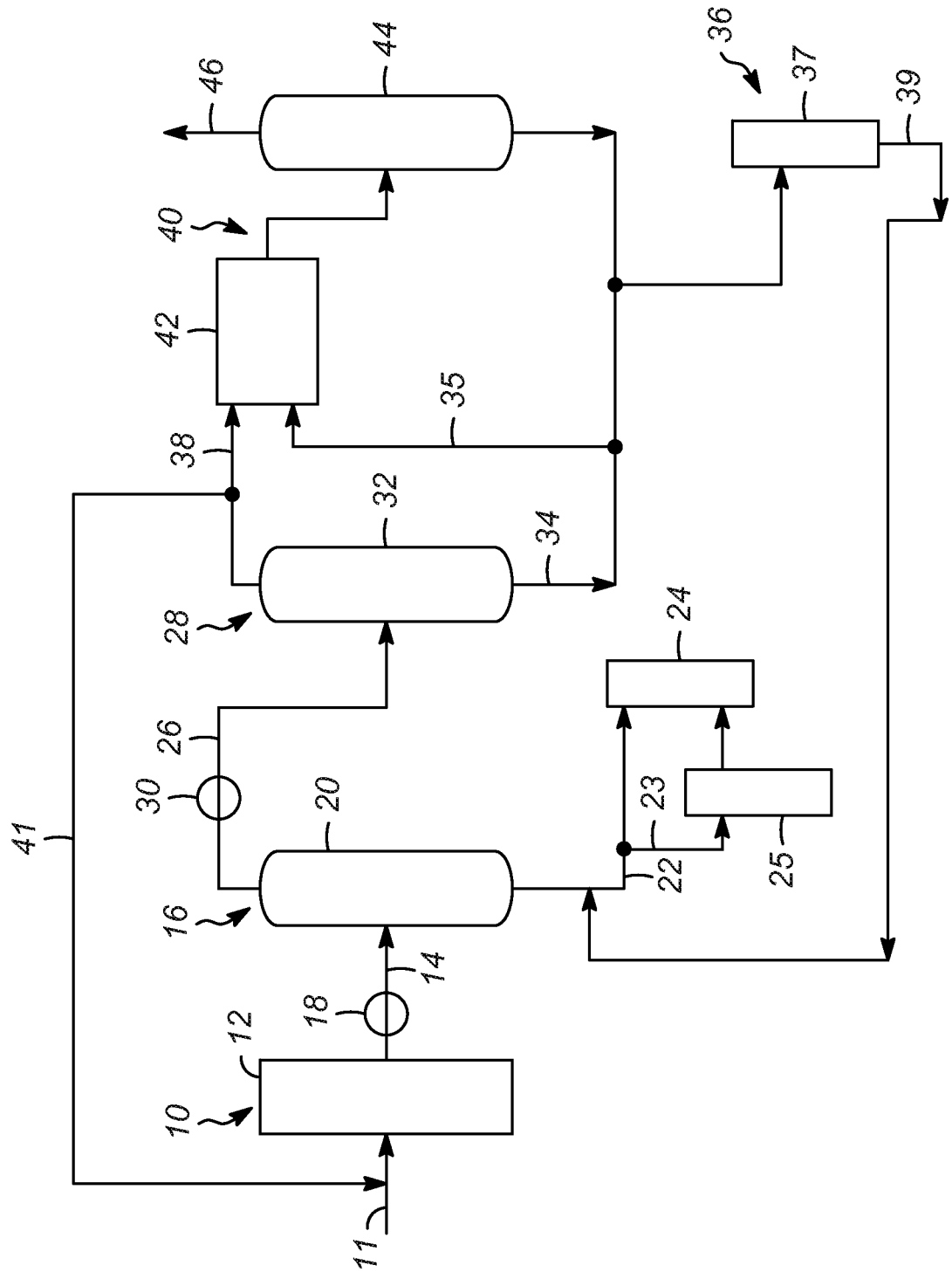

PROCESS FOR SEPARATING BENZENE FROM A REACTOR EFFLUENT

BACKGROUND OF THE INVENTION

The demand for clean and safe transportation fuel is increasing worldwide. This increased demand is, in part, a result of government regulations in various countries which attempt to reduce and/or eliminate certain chemicals that are typically contained in the transportation fuel. These government regulations can impose challenges on fuel refiners and producers to provide transportation fuel which contains lower amounts of the specified chemicals in order to comply with the various governmental regulations.

In the United States, a recent example of this is the Mobile Source Air Toxics 2 (MSAT2) benzene control program. Benzene is a byproduct of one or more chemical reactions in the reforming process associated with the refining of light petroleum distillate. Beginning in 2011, the MSAT2 regulations limit the level of benzene, a known carcinogen, in gasoline sold in the United States to an average of 0.62% of the total liquid volume of the gasoline.

It is believed that a typical reforming process might result in a reformate that has approximately 10% or less by weight of benzene. Generally, in a reforming process light petroleum distillate is contacted with catalyst in the presence of hydrogen at high temperatures to produce a high-octane liquid effluent that is rich aromatic compounds. Typically, there are a series of reactors in which the feedstock passes. After a reactor effluent from the last reactor is cooled, it is typically sent to a separator where a part of overhead vapor can be compressed and recycled to the reactor. The remaining reactor effluent can be sent to a product recovery section which includes passing the reactor effluent through various processing units and separating units some of which are designed to remove the benzene from the reactor effluent.

While current processes may be successful at obtaining appropriate benzene levels in separation steps of the entire process, the current methods require large amounts of heat and energy input. Additionally such methods typically also require large equipment sizes.

Additionally, competition in the gasoline refining industry constantly demands development of more energy efficient processing technology and methods—especially technology and methods that can competitively meet the current requirements.

Finally, beyond the current standards, future government regulations may further limit the amount of benzene in gasoline to an even lower level—creating a greater challenge for refiners and producers.

Therefore, it would be desirable to have a process that can effectively and efficiently separate benzene from a reactor effluent.

SUMMARY OF THE INVENTION

Accordingly, in an embodiment of the present invention, a method for separating benzene from a reactor effluent is provided in which a reactor effluent is recovered from a reaction zone. The reactor effluent includes at least benzene. The reactor effluent is passed to a first separation zone to separate the reactor effluent into an overhead stream and a bottom stream. It is contemplated that the reactor effluent is cooled prior to passing from the reactor effluent to the first separation zone.

The first separation zone has an operating temperature. In some embodiments of the present invention, it is contemplated that the operating temperature of the first separation zone is between 65° C. to 130° C., and preferably between 85° C. to 110° C.

In some embodiments of the present invention, a temperature of the reactor effluent as it is passed to the first separation zone is measured. Based upon the temperature of the reactor effluent, the operating temperature of the first separation zone may be adjusted.

The overhead stream from the first separation zone is recovered from the first separation zone and cooled to produce a cooled overhead stream. The cooled overhead stream is passed to a second separation zone to separate the cooled overhead stream into a benzene rich bottom stream and a second overhead stream.

The second separation zone has an operating temperature lower than the operating temperature of the first separation zone.

The benzene rich bottom stream from the second separation zone may be recovered and passed to a debutanizer or a recontact zone or both.

It is further contemplated to recover the second overhead stream from the second separation zone and pass it to a recontact zone. In the recontact zone, the second overhead stream is separated into a recontact light stream and a recontact bottom stream. The recontact bottom stream may be recovered from the recontact zone and passed to a debutanizer.

In other embodiments of the present invention, a method for separating benzene from a reactor effluent is provided in which a naphtha feedstock is reacted in the presence of a catalyst in a reaction zone to produce a reactor effluent. Again, the reactor effluent includes at least benzene. The reactor effluent is recovered from the reaction zone and passed to a first separation zone.

In the first separation zone, the reactor effluent is separated into an overhead stream and a bottom stream. Again, the first separation zone may have an operating temperature between 65° C. to 130° C., and preferably between 85° C. to 110° C., and an operating pressure between approximately 345 to 689 KPa (approximately 50 to 100 psi). In a preferred embodiment of the present invention, a temperature of the reactor effluent is measured, and an operating temperature of the first separation zone is controlled and adjusted based upon the temperature of the reactor effluent.

The bottom stream includes mostly hydrocarbons containing seven carbons or more. The bottom stream is recovered from the first separation zone.

The overhead stream from the first separation zone includes mostly hydrocarbons containing six carbons or less. The overhead stream is also recovered from the first separation zone and may be cooled to a temperature of approximately 40° C. to produce a cooled overhead stream. Thereafter, the cooled overhead stream is passed to a second separation zone.

In the second separation zone, the cooled overhead stream is separated into a benzene rich bottom stream and a second overhead stream. In some embodiments, the first separation zone has an operating temperature that is higher than the operating temperature of the second separation zone.

It is further contemplated that the second overhead stream is recovered from the second separation zone and passed to a recontact zone. In the recontact zone, the second overhead stream is compressed and separated into a recontact light stream and a recontact bottom stream. The recontact zone may have an operating pressure between approximately 2760 to 3450 KPa (approximately 400 to 500 psi). The recontact bottom stream may be recovered from the recontact zone and passed to a debutanizer. Additionally, the recontact light stream may also be recovered from the recontact zone and passed to a hydrogen purification unit.

In one or more embodiments of the present invention, the benzene rich bottom stream includes approximately 80% of a total benzene amount in the reactor effluent. It is contemplated that the bottom stream of the first separation zone includes less than 15% of a total benzene amount in the reactor effluent and preferably between approximately 5 to 10% of a total benzene amount in the reactor effluent.

DETAILED DESCRIPTION OF THE DRAWING

The drawing is simplified process flow diagram in which:
The FIGURE shows a process flow diagram of process according to one or more embodiments of the present invention for separating benzene from a reactor effluent.

DETAILED DESCRIPTION OF THE INVENTION

A process has been developed for separating benzene which includes two separation zones, one operating at a higher temperature than the other. A first bottom stream, being a benzene lean stream, can be recovered from the reactor effluent in the first separation zone. A second stream, being a benzene rich stream, is recovered from the second separation zone.

It is believed that one or more of the embodiments of the present invention described herein are beneficial and desirable for a number of reasons.

For example, the use of the first separation zone to produce a benzene lean stream provides a stream that contains sufficiently low concentrations of benzene that it can it can be passed to a gasoline blending pool without requiring treatment/separation to remove the benzene from the stream. It is believed that at least 50% of the reactor effluent will be included in the benzene lean stream, which has been recovered without requiring additional heat or energy to the process to remove the benzene from same.

Additionally, the use of the second separation zone to provide a benzene rich stream, having between 80 to 90% of the total benzene in the reactor effluent, will minimize the volume of material that needs to be passed to a debutanizer, for example, to treat the reactor effluent to reduce the benzene content in same. As will be appreciated, since the volume of material passed to the debutanizer is lessened, the size of the debutanizer necessary can be reduced. Similarly, the size of a recontact drum in the recontact zone may likewise be reduced for the same reasons.

Moreover, in addition to the capital expenditure savings associated with providing smaller components in the various zones, the smaller components will also provide operating expenditure savings by, for example, requiring less energy input and requiring less heat.

Also, controlling the temperature of the first separation zone is believed to allow for adjustments to the amount of benzene in the benzene lean stream. This will allow the concentration of benzene in the gasoline blending pool to be adjusted based upon the requirements of a refiner.

As shown in the Figure, a reaction zone 10 is provided in which a feedstock is reacted in the presence of a catalyst to produce a reactor effluent which contains, among other compounds, benzene.

In the context of the present invention it is contemplated, but not necessarily required, that the reaction zone 10 includes a reforming reactor 12 in which naphtha feedstock is passed via a line 11. In the reforming reactor 12 the naphtha feedstock is reacted in the presence of a catalyst to produce a reactor effluent. More specifically, a naphtha feed is combined with hydrogen (preferably recycled hydrogen). The mixture is heated and is passed to the reactor 12 where it flows across various beds containing, among other things, a catalyst. The mixture will flow vertically downward as a result of gravity. The components of the naphtha feedstock undergo various reactions wherein paraffins and naphthenes are reacted into molecules with a higher octane number. However, in addition to producing the desired products, these reactions also produce less desirable products, at least with respect to producing reformate for gasoline blending pools. The entire volume of the chemicals produced in the reaction zone 10 make up the reactor effluent.

In known systems, as described for example in U.S. Pat. Pub. No. 2013/0193034, the reactor effluent is sent to a separator where a hydrogen light stream and a heavy bottom stream are recovered. However, instead of separating the benzene, U.S. Pat. Pub. No. 2013/0193034 teaches to recycle a portion of the reformate to drive the reaction to produce more hydrogen, and, according to that document, reduce the amount of benzene in the reactor effluent. However, such a design has a high amount of energy consumption compared to the embodiments of the present invention because it requires benzene to be separated in a downstream separation zone.

In the present invention, as depicted in the Figure, the reactor effluent is recovered from the reaction zone 10 and passed via a line 14 to a first separation zone 16. Since the reactor effluent typically has a temperature between 475° C. to 525° C., it is preferred that prior to reaching the first separation zone 16, the reactor effluent is cooled. It is preferred that the temperature of the reactor effluent is between 65° C. to 130° C. when the reactor effluent is reaches the first separation zone 16. The cooling can be accomplished with a product cooler 18, with the heat recovered from same being used elsewhere in the process.

The first separation zone 16 preferably includes a separator 20. As will be appreciated by those of ordinary skill in the art, the separator 20 is typically a fractionation column which may comprise a vessel with a number of trays, for example between 2 to 5 trays.

It is preferred that the first separation zone 16 is operated at a temperature in the range of 65° C. to 130° C., and most preferably in the range of 85° C. to 110° C. Additionally, the first separation zone 16 is operated at a pressure preferably between approximately 345 to 689 KPa (approximately 50 to 100 psi).

It is also preferred that the temperature of the reactor effluent is measured to allow for adjustment and control of the operating temperature of the first separation zone 16.

Within the first separation zone 16, the reactor effluent is separated into an overhead stream and a bottom stream. The overhead stream comprises most of the hydrocarbons containing six carbons or less from the reactor effluent. The bottom stream comprises most of the hydrocarbons containing seven carbons or more and preferably contains less than 15% of the total amount of benzene in the reactor effluent. In a preferred embodiment, the bottom stream contains between 5 to 10% of the total amount of benzene, and in a most preferred embodiment also contains less than 1% by weight of hydrocarbons with four carbons or less. As will be appreciated by those of ordinary skill in the art, when separating hydrocarbons, there typically can be some crossover between the various fractions/streams during the separation processes and thus, the present invention is intended to accommodate the crossover amounts of compounds.

Since the first separation zone 16 has separated most of the benzene from the bottom stream, there is no need to pass the bottom stream to a processing zone to remove or reduce the benzene content further. Rather, the bottom stream already meets the minimum requirements for mixing in a gasoline blending pool. Accordingly, in a preferred embodiment, the bottom stream is recovered by a line 22, and may be passed directly, for example, to a gasoline blending pool 24. Alternatively, the bottom stream may be passed via a line 23 to a reformate splitter 25, and the resultant splits passed to the gasoline blending pool 24.

Returning to the first separation zone 16, the overhead stream from the first separation zone 16 may also be recovered. Accordingly, it may be passed via a line 26 to a second separation zone 28. In a preferred embodiment, the overhead stream is cooled in the line 26 as it is passed to the second separation zone 28 and thus is a cooled overhead stream. Most preferably the cooled overhead stream is at ambient temperature (approximately 40° C. to 50° C.). Again, the cooling can be accomplished with a product cooler 30, with the heat recovered from same being used elsewhere in the process.

The second separation zone 28 may also include a second separator 32. Again, as is known, the second separator 32 is typically a fractionation column which may comprise a vessel with a number of trays, for example between 2 to 5 trays.

The second separation zone 28 has an operating temperature that is lower that the operating temperature of the first separation zone 16. The second separation zone 28 also operates at a pressure preferably between approximately 345 to 689 KPa (approximately 50 to 100 psi).

Within the second separation zone 28, the cooled overhead stream is separated into a benzene rich bottom stream and a second overhead stream. The benzene rich bottom stream will contain at least 80%, and preferably at least 90% of the total amount of benzene in the reactor effluent.

The benzene rich bottom stream may be recovered via a line 34 and passed to a processing zone 36, which may include a debutanizer 37.

In the debutanizer 37, the benzene rich bottom stream is separated with a first overhead stream, a second overhead stream, and a bottom stream. The first overhead stream is a vapor stream comprising hydrocarbons with three carbons or less and hydrogen. The second overhead stream is a liquid stream comprising hydrocarbons having three or four carbons. The bottom stream comprises benzene and can be removed via a line 39 and passed either to the reformate splitter 25 or the gasoline blending pool 24.

Since the benzene rich bottom stream has a higher concentration of benzene compared with a conventional benzene separation processes, the work load of the further processing unit 36 may be reduced by up to 50%, and the size of the unit 36 may likewise be reduced based upon the reduction in the amount of material being passed to same.

Instead of passing to the further processing unit 36, the benzene rich bottom stream may alternatively be passed to a recontact zone 40 via a line 35. The recontact zone 40 is discussed below.

Returning to the second separation zone 28, the second overhead stream may be recovered and passed via a line 38 to a recontact zone 40 having a recontact section 42 and a recontact drum 44. A portion of the second overhead stream may also be passed via a line 41 to the reaction zone 10.

In the recontact section 42 of the recontact zone 40, the second overhead stream is compressed at high pressure in one or more stages, cooled after each compression stage to separate out a liquid phase and a vapor phase. The net liquid phase and the net vapor phase from all of the compression/cooling stages are passed to the recontact drum 42.

In the recontact drum 42 of the recontact zone 40, the second overhead stream will be separated into a recontact light stream and a recontact bottom stream. Typically, at high pressure, the recontact bottom stream comprises hydrocarbons having at least five carbons and the hydrogen recovery in the recontact light stream will be higher and more pure. The recontact zone 40 is preferably operated at ambient temperature, and at a pressure that is between approximately 2760 to 3450 KPa (approximately 400 to 500 psi).

The recontact light stream may also be recovered via a line 46 and passed to a further processing unit, for example, a hydrogen purification unit.

A simulation for a 276,691 kg/kr (611,000 lb/hr) naphtha feed encompassing various embodiments of the present invention was conducted. The results of the simulation are shown below in Table 1.

| Stream | Reactor effluent to first separator | Lean Benzene from first separator | Rich Benzene from second separator |
|---|---|---|---|
| Temperature | 88° C. (190° F.) | 88° C. (190° F.) | 38° C. (100° F.) |
| Pressure | 345 kPa (50 psi) | | |
| Flow rate | 356,428 kg/hr (785,789 lb/hr) | 126,228 kg/hr (278,286 lb/hr) | 102,469 kg/hr (225,905 lb/hr) |
| Benzene content | 9,637 kg/hr (21,246 lb/hr) | 1,499 kg/hr (3304 lb/hr) | 8,138 kg/hr (17,942 lb/hr) |

As can be seen in Table 1, the simulation resulted in a benzene lean stream which included 15% of the total benzene of the reactor effluent and a benzene rich stream which included 85% of the total benzene of the reactor effluent.

As will be appreciated, a process according to one or more of these embodiments provides an effective and efficient method to separate benzene from a reaction effluent.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

What is claimed is:

1. A method for separating benzene from a reactor effluent, the method comprising:
   recovering a reactor effluent from a reaction zone, wherein the reactor effluent includes hydrocarbons having between four and seven hydrocarbons and further includes benzene;
   passing the reactor effluent to a first separation zone to separate the reactor effluent into an overhead stream including hydrocarbons having six carbons or less and a bottom stream including hydrocarbons having seven carbon atoms or more and comprising less than 15% of a total benzene amount in the reactor effluent, the first separation zone having an operating temperature of between about 65° C. to 130° C.;

cooling the overhead stream of the first separation zone to produce a cooled overhead stream;

passing the cooled overhead stream to a second separation zone to separate the cooled overhead stream into a benzene rich bottom stream comprising at least 80% of the total amount of benzene in the reactor effluent and a second overhead stream, the second separation zone having an operating temperature lower than the operating temperature of the first separation zone, the second separation zone having a temperature of between about 40° C. to about 50° C.; and passing at least a portion of the benzene rich bottom stream from the second separation zone to a debutanizer.

2. The method of claim 1 wherein the bottom stream of the first separation zone comprises between approximately 5 to 10% of a total benzene amount in the reactor effluent.

3. The method of claim 1 wherein the cooled overhead stream is at ambient temperature.

4. The method of claim 1 further comprising:
measuring a temperature of the reactor effluent; and,
adjusting the operating temperature of the first separation zone based upon the temperature of the reactor effluent.

5. The method of claim 1 further comprising:
passing remaining portion of the benzene rich bottom stream from the second separation zone to a recontact zone.

6. The method of claim 1 further comprising:
passing the second overhead stream to a recontact zone;
separating the second overhead stream into a recontact light stream and a recontact bottom stream; and,
passing the recontact bottom stream to a debutanizer.

7. The method of claim 1 wherein the benzene rich bottom stream comprises approximately, 90% of a total benzene amount in the reactor effluent.

8. The method of claim 1 further comprising:
cooling the reactor effluent prior to passing the reactor effluent to the first separation zone.

9. A method for separating benzene from a reactor effluent, the method comprising:
reacting a naphtha feedstock in the presence of a catalyst in a reaction zone to produce a reactor effluent, wherein the reactor effluent includes hydrocarbons having between four and seven hydrocarbons and further including benzene;
passing the reactor effluent from the reaction zone to a first separation zone having an operating temperature of between about 65° C. to about 130° C.;

separating the reactor effluent in the first separation zone into an overhead stream and a bottom stream, the overhead stream comprising hydrocarbons containing six carbons or less, and the bottom stream comprising hydrocarbons containing seven carbons or more and containing less than 15% of a total amount of benzene and containing less than 1% by weight hydrocarbons with four carbons or less;

passing the bottom stream to a gasoline blending pool without separation to remove benzene;

cooling the overhead stream of the first separation zone to a temperature of approximately 40° C. to produce a cooled overhead stream;

passing the cooled overhead stream to a second separation zone; and, separating the cooled overhead stream in the second separation zone into a benzene rich bottom stream comprising at least 80% of the total amount of benzene in the reactor effluent and a second overhead stream, the second separation zone having an operating temperature lower than the operating temperature of the first separation zone, the second separation zone having a temperature of about 40° C. to about 50° C.; and passing at least a portion of the benzene rich bottom stream from the second separation zone to a debutanizer.

10. The method of claim 9, wherein the first separation zone has an operating pressure between approximately 345 to 689 KPa.

11. The method of claim 9, further comprising:
measuring a temperature of the reactor effluent; and,
adjusting an operating temperature of the first separation zone based upon the temperature of the reactor effluent.

12. The method of claim 9 wherein the benzene rich bottom stream comprises approximately 90% of the total amount of benzene in the reactor effluent.

13. The method of claim 9 further comprising:
passing the second overhead stream to a recontact zone;
compressing and separating the second overhead stream in the recontact zone into a recontact light stream and a recontact bottom stream, the recontact zone having an operating pressure between approximately 2760 to 3450 KPa; and,
passing the recontact bottom stream to a debutanizer.

14. The method of claim 13 further comprising:
passing the recontact light stream to a hydrogen purification unit.

* * * * *